US010993683B2

(12) United States Patent
Hosoki et al.

(10) Patent No.: US 10,993,683 B2
(45) Date of Patent: *May 4, 2021

(54) RADIATION IMAGING APPARATUS AND RADIATION IMAGING SYSTEM

(71) Applicant: Konica Minolta, Inc., Tokyo (JP)

(72) Inventors: Tetsu Hosoki, Koganei (JP); Tomonori Gido, Kawasaki (JP); Nobuyuki Miyake, Yokohama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/741,122

(22) Filed: Jan. 13, 2020

(65) Prior Publication Data

US 2020/0146643 A1    May 14, 2020

Related U.S. Application Data

(63) Continuation of application No. 15/346,924, filed on Nov. 9, 2016, now Pat. No. 10,568,595.

(30) Foreign Application Priority Data

Dec. 4, 2015 (JP) .................................. 2015-237102

(51) Int. Cl.
*A61B 6/00* (2006.01)
*H04N 5/32* (2006.01)

(52) U.S. Cl.
CPC .......... *A61B 6/4405* (2013.01); *A61B 6/4233* (2013.01); *A61B 6/54* (2013.01); *H04N 5/32* (2013.01)

(58) Field of Classification Search
CPC ........ A61B 6/4233; A61B 6/4405; A61B 6/54
See application file for complete search history.

(56) References Cited

U.S. PATENT DOCUMENTS 4,562,464 A    12/1985    Kurihara
6,271,880 B1    8/2001    Kameshima
(Continued)

FOREIGN PATENT DOCUMENTS

EP    1642528 A1    4/2006
JP    2006122667 A    5/2006
(Continued)

OTHER PUBLICATIONS

Extended European Search Report dated Mar. 29, 2017 from corresponding European Application No. 16201879.0-1903; 9 pages.
(Continued)

*Primary Examiner* — Chih-Cheng Kao
(74) *Attorney, Agent, or Firm* — Lucas & Mercanti, LLP

(57) ABSTRACT

A portable radiation imaging apparatus including: a detection section which includes a plurality of radiation detection elements for accumulating electric charges corresponding to a radiation amount, the radiation detection elements being two-dimensionally arranged; and a control section which controls accumulation of the electric charges in the radiation detection elements and reading of the accumulated electric charges from the radiation detection elements and generates a plurality of frame images of a subject, the electric charges to be accumulated corresponding to the radiation amount of radiation emitted in a pulsed manner by a radiation source and transmitted through the subject, wherein the control section adjusts a synchronization timing between the radiation source and the detection section by using a waveform of radiation emitted by the radiation source, the waveform being obtained by reading electric charges from at least a part of the plurality of radiation detection elements.

9 Claims, 6 Drawing Sheets

(56) References Cited

U.S. PATENT DOCUMENTS

| | | | |
|---|---|---|---|
| 10,568,595 B2 * | 2/2020 | Hosoki | H04N 5/32 |
| 2011/0013746 A1 | 1/2011 | Zeller | |
| 2012/0018640 A1 | 1/2012 | Shimizukawa et al. | |
| 2014/0110595 A1 | 4/2014 | Iwakiri | |

FOREIGN PATENT DOCUMENTS

| | | |
|---|---|---|
| JP | 2010081960 A | 4/2010 |
| JP | 2014-161690 A | 9/2014 |
| WO | 2013015350 A1 | 1/2013 |

OTHER PUBLICATIONS

JPO, Notification of Reasons for Refusal from corresponding Japanese Patent Application No. 2015-237102 dated Aug. 27, 2019; 7 pages.

JPO, Office Action for the related Japanese Patent Application No. 2020-030287, dated Mar. 23, 2021, with English translation.

* cited by examiner

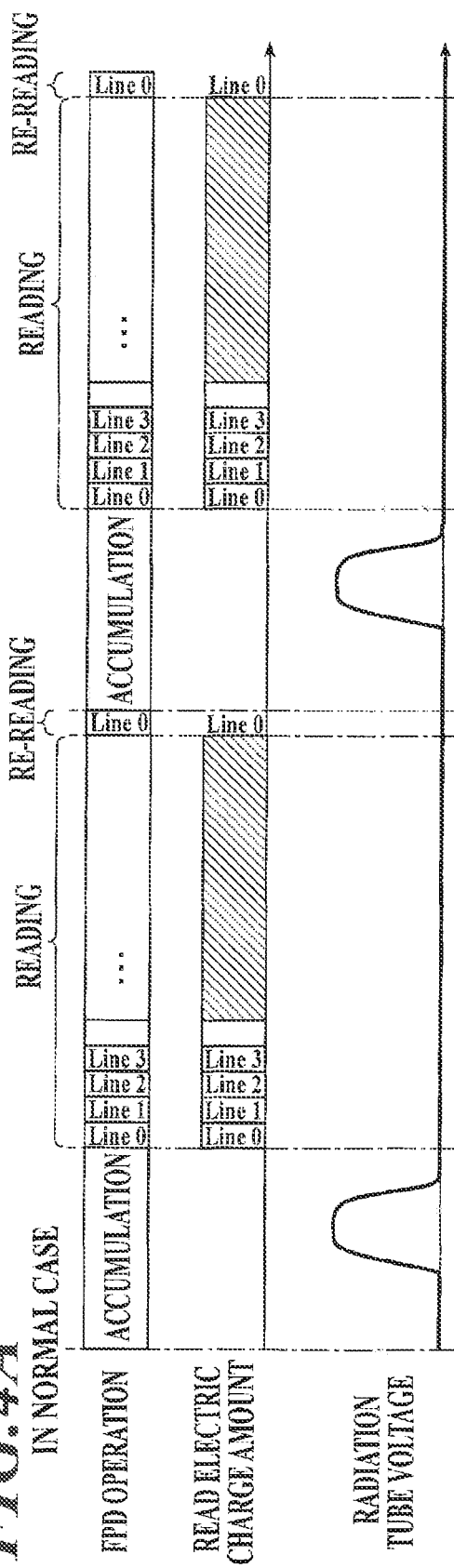
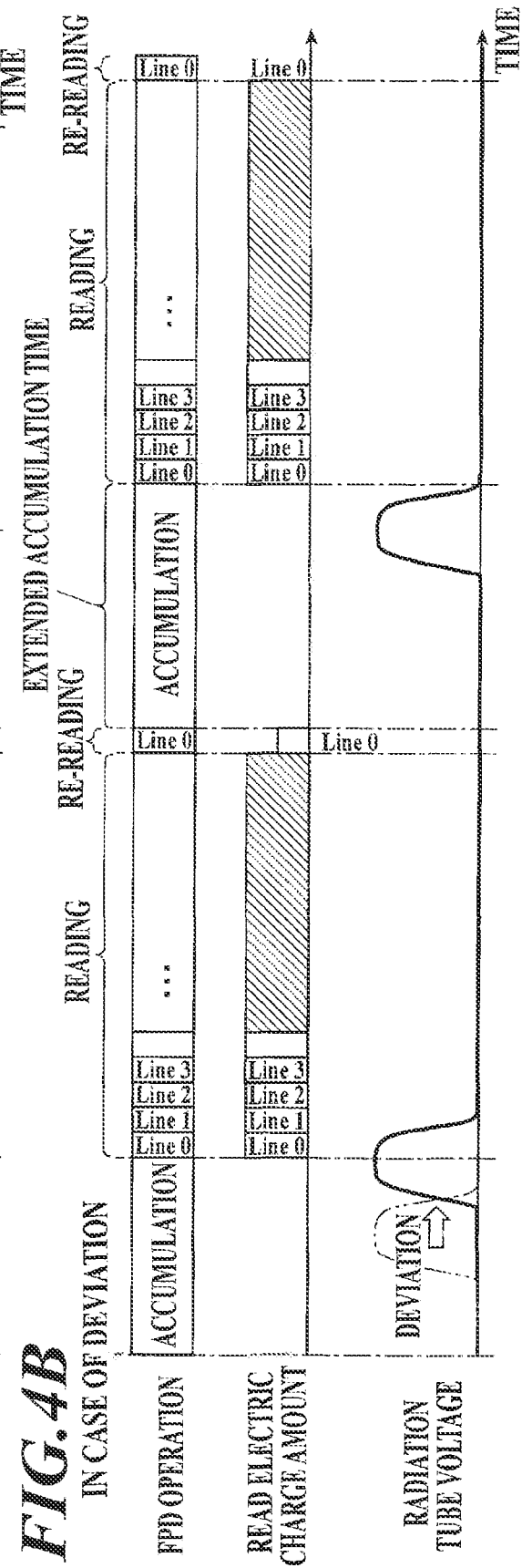
FIG. 4A IN NORMAL CASE
FIG. 4B IN CASE OF DEVIATION

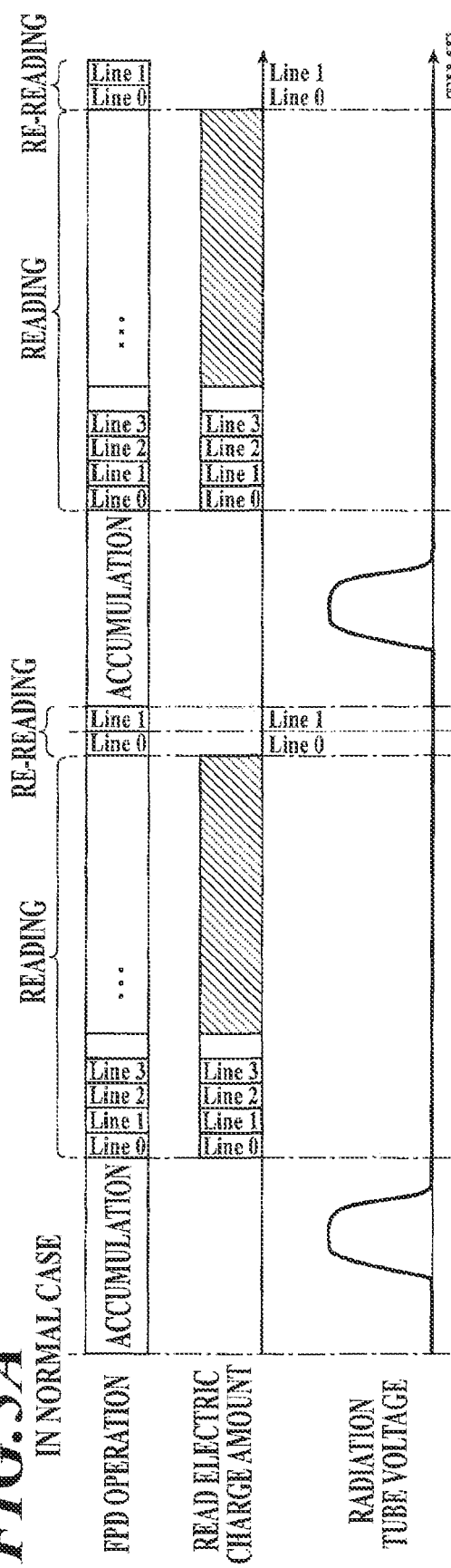
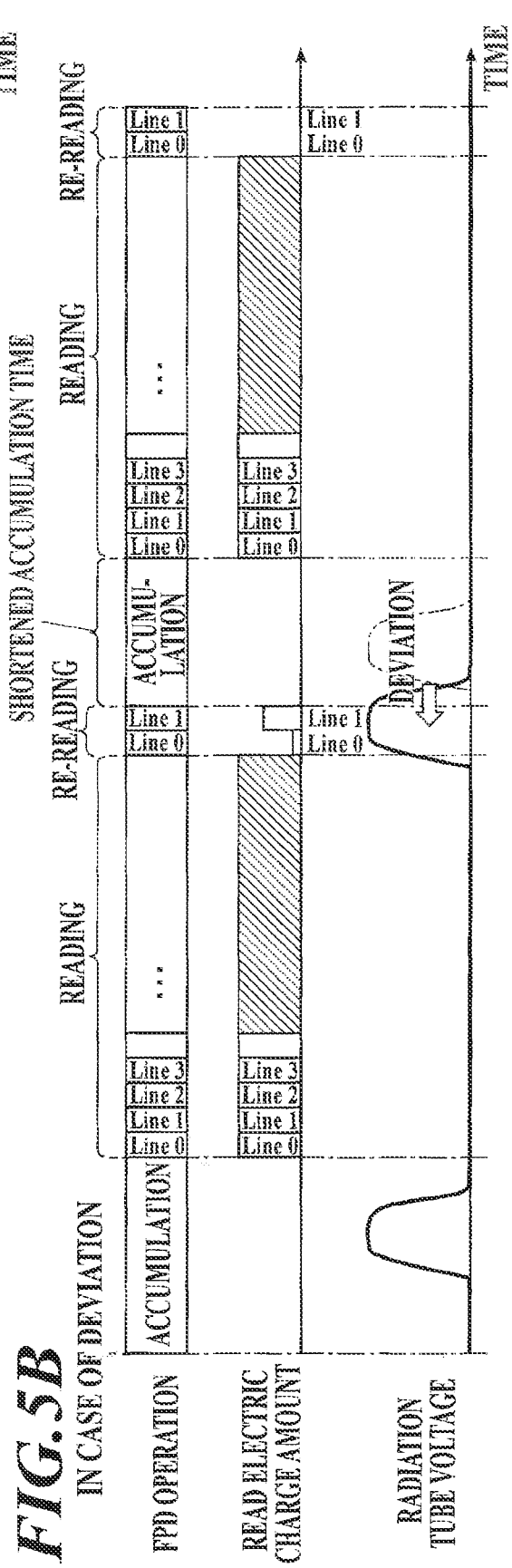

RADIATION IMAGING APPARATUS AND RADIATION IMAGING SYSTEM

CROSS-REFERENCE TO RELATED APPLICATIONS

This application is a continuation of U.S. patent application Ser. No. 15/346,924, filed on Nov. 9, 2016, which claimed the priority of Japanese Application No. 2015-237102 filed on Dec. 4, 2015, the priority of both applications is claimed and the entire content of both applications are hereby incorporated by reference.

BACKGROUND OF THE INVENTION

1. Field of the Invention

The present invention relates to a radiation imaging apparatus and a radiation imaging system.

2. Description of Related Art

In recent years, there have been known radiation imaging systems using portable radiation imaging apparatuses (such as an FPD (Flat Panel Detector)) each of which includes two-dimensionally arranged radiation detection elements for accumulating electric charges corresponding to radiation emitted from a radiation source and transmitted through a subject and reads out the electric charges accumulated in the radiation detection elements to generate image data. Such radiation imaging systems require synchronization between a radiation emission period for emitting radiation in the radiation source and an electric charge accumulation period for accumulating electric charges in the radiation imaging apparatus in order to perform the radiation emission by the radiation source during the electric charge accumulation period.

However, in a case where a radiation imaging apparatus wirelessly communicates with a radiation control apparatus which controls a radiation source, due to a problem in real time property, the synchronization is possibly not achieved by performing synchronized communication for each radiation emission between the radiation control apparatus and the radiation imaging apparatus when performing dynamic imaging of emitting pulsed-radiation (pulse emission) at a predetermined time interval and obtaining a plurality of frame images.

Thus, for example, Patent document 1 (Patent Application Laid Open Publication No. 2010-81960) describes a technique of providing a time measurement section to measure time in a console as a radiation control apparatus which performs imaging instruction, further providing a time measurement section to measure time which is synchronized with the time measurement section of the console to an electronic cassette containing an FPD therein, controlling each of the time measurement sections to measure time, emitting radiation from a radiation source for a predetermined period of time from exposure start time which was determined in advance in the console, and generating image data indicating a radiation image by reading out electric charges accumulated in the FPD after the predetermined period of time elapses from the exposure start time in the electronic cassette.

However, in many cases, the portable radiation imaging apparatus is used in environment such as between a patient and a bed in which heat is kept and temperature easily rises. Thus, the heat release may not be sufficiently ensured in the portable radiation imaging apparatus. On the other hand, the radiation control apparatus naturally releases sufficient heat with respect to the heat generation amount even during operation, and thus the influence of heat generation is negligible. Thus, even when the clocks are synchronized between the radiation control apparatus and the radiation imaging apparatus in advance, the radiation emission period and electric charge accumulation period may be out of synchronization (synchronization deviation may be generated) in some cases due to the influence of change in oscillator operation frequency caused by the temperature rise of the radiation imaging apparatus.

Also in a case where fluctuation is generated in the output of radiation emitted from the radiation source, the radiation emission period and the electric charge accumulation period may be out of synchronization.

In a case where the synchronization deviation is generated at dynamic imaging to generate a plurality of frame images and radiation is emitted also during a reading period after the electric charge accumulation period ends, for example, there remain electric charges corresponding to the radiation emitted in the reading period, and thus deterioration in image quality is generated in the next frame image.

SUMMARY OF THE INVENTION

An object of the present invention is to suppress deterioration of image quality caused by the synchronization deviation between the radiation emission period in the radiation source and the electric charge accumulation period in the radiation imaging apparatus.

In order to solve the above problems, according to one aspect of the present invention, there is provided a portable radiation imaging apparatus including: a detection section which includes a plurality of radiation detection elements for accumulating electric charges corresponding to a radiation amount, the radiation detection elements being two-dimensionally arranged; and a control section which controls accumulation of the electric charges in the radiation detection elements and reading of the accumulated electric charges from the radiation detection elements and generates a plurality of frame images of a subject, the electric charges to be accumulated corresponding to the radiation amount of radiation emitted in a pulsed manner by a radiation source and transmitted through the subject, wherein the control section adjusts a synchronization timing between the radiation source and the detection section by using a waveform of radiation emitted by the radiation source, the waveform being obtained by reading electric charges from at least a part of the plurality of radiation detection elements.

According to another aspect of the present invention, there is provided a radiation imaging system including: a radiation source which is capable of pulse emission; and the above radiation imaging apparatus.

BRIEF DESCRIPTION OF THE DRAWINGS

The above and other objects, advantages and features of the present invention will become more fully understood from the detailed description given hereinafter and the appended drawings which are given by way of illustration only, and thus are not intended as a definition of the limits of the present invention, and wherein:

FIGS. 4A and 4B are views each showing examples of the operation of FPD cassette, read electric charge amount and radiation tube voltage when a line L0 (Line 0) is re-read after the end of reading electric charges in radiation detection elements for generating a frame image;

FIGS. 5A and 5B are views each showing examples of operation of FPD cassette, read electric charge amount and radiation tube voltage when the line L0 (Line 0) and line L1 (Line 1) are re-read after the end of reading electric charges in radiation detection elements for generating a frame image;

DETAILED DESCRIPTION OF THE PREFERRED EMBODIMENT

First Embodiment (Configuration of Radiation Imaging System 100)

First, the configuration of a first embodiment according to the present invention will be described.

Figure 1:
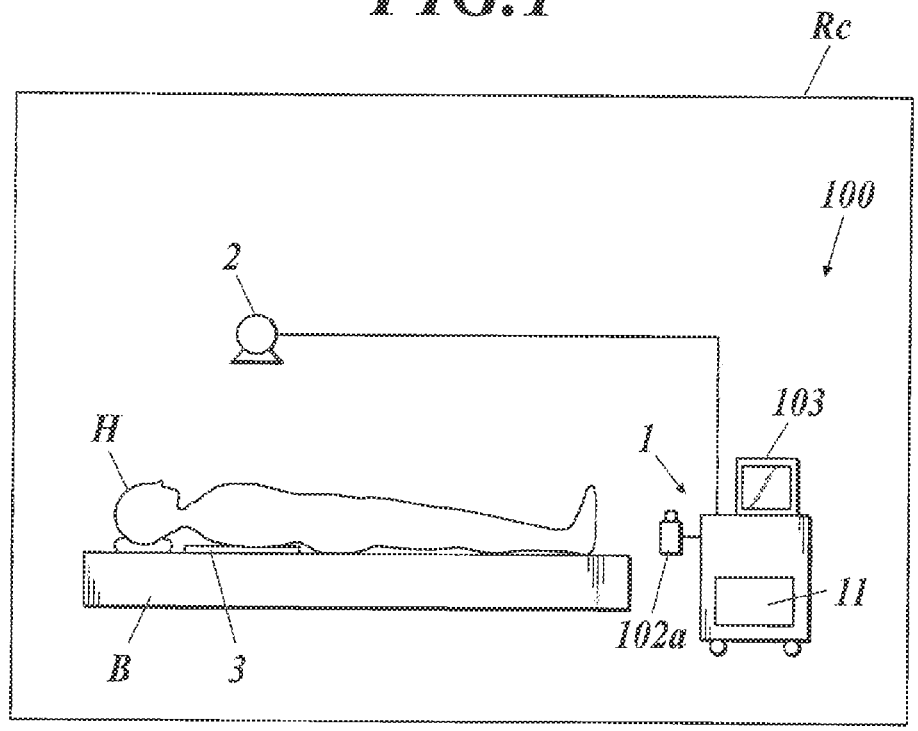
FIG. 1 is a view showing an entire configuration example of a radiation imaging system in an embodiment.

FIG. 1 shows an entire configuration example of a radiation imaging system 100 in the embodiment.

The radiation imaging system 100 is, for example, a system for doctor's rounds to perform radiation imaging to patients who cannot move easily, and configured by including a radiation control apparatus 1, a radiation source 2 and an FPD (Flat Panel Detector) cassette 3. The radiation control apparatus 1 has wheels and is configured as a mobile cart for doctor's rounds which is capable of moving.

As shown in FIG. 1, the radiation imaging system 100 is a system which is brought into an operating room, an intensive care unit, a hospital room Rc and such like, and performs dynamic imaging of a subject H by emitting radiation from the radiation source 2 while the FPD cassette 3 is inserted, for example, between a bed B and the subject H lying on the bed B or into an insertion opening (not shown in the drawings) provided in the bed B on the opposite side to the subject H. In the embodiment, the dynamic imaging is obtaining a dynamic image by repeatedly emitting pulsed radiation such as X-ray (pulse emission) to the subject H at a predetermined time interval in response to one imaging operation (operation of exposure switch 102a). A series of images obtained by the dynamic imaging is referred to as a dynamic image. Each image in the plurality of images forming the dynamic image is referred to as a frame image.

Hereinafter, apparatuses forming the radiation imaging system 100 will be described.

Figure 2:
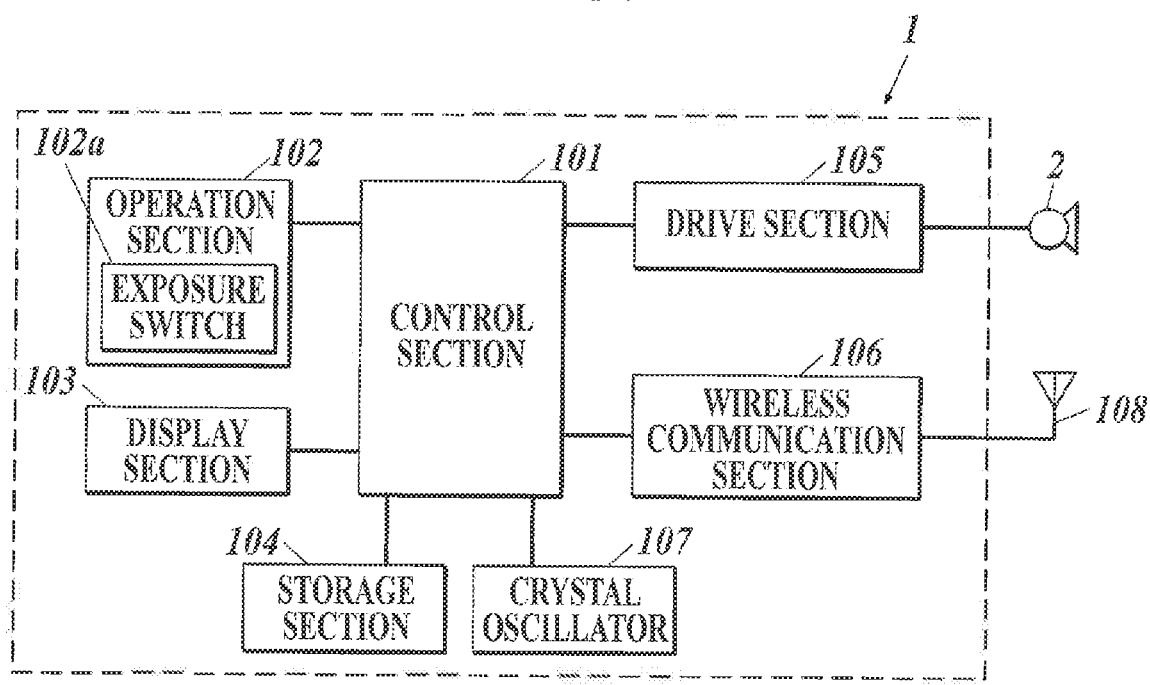
FIG. 2 is a block diagram showing a functional configuration of a radiation control apparatus.

The radiation control apparatus 1 is an apparatus which controls the radiation source 2 to emit radiation on the basis of radiation emission conditions which were input. As shown in FIG. 2, the radiation control apparatus 1 is configured by including a control section 101, an operation section 102, a display section 103, a storage section 104, a drive section 105, a wireless communication section 106, a crystal oscillator 107 and such like.

The control section 101 is configured by including a CPU (Central Processing Unit), a RAM (Random Access Memory) and such like. The CPU of the control section 101 reads out system programs and various types of processing programs stored in the storage section 104 to load them into the RAM according to the operation of the operation section 102 and controls the operations of the sections in the radiation control apparatus 1 according to the loaded programs.

The operation section 102 has a touch panel or the like with transparent electrodes disposed in a reticular pattern so as to cover the surface of the display section 103, detects the position pressed bya finger, a touch pen or the like, and outputs the positional information as operation information to the control section 101.

The operation section 102 also includes the exposure switch 102a for an imaging operator to instruct exposure of radiation. The exposure switch 102a is a two-step switch.

The display section 103 is configured by including a monitor such as an LCD (Liquid Crystal Display) and a CRT (Cathode Ray Tube), and performs display according to an instruction of display signal input from the control section 101.

The storage section 104 is configured by including a non-volatile semiconductor memory, a hard disk and such like. The storage section 104 stores data such as various programs executed by the control section 101, parameters necessary for executing processing of the programs and the processing results.

The drive section 105 is a circuit for driving an X-ray tube or the like of the radiation source 2. The drive section 105 is connected to the radiation source 2 via a cable.

The wireless communication section 106 includes an antenna 108, and performs wireless communication with external equipment such as the FPD cassette 3.

The crystal oscillator 107 is an element which oscillates by piezoelectric effect, and the oscillation number is input to the CPU of the control section 101. The control section 101 measures time on the basis of the oscillation number input from the crystal oscillator 107.

The radiation source 2 is capable of pulse emission and emits radiation (X-ray) to the subject H in accordance with control of the radiation control apparatus 1.

The FPD cassette 3 is a portable radiation imaging apparatus capable of dynamic imaging. Hereinafter, the FPD cassette 3 is described as an indirect type apparatus which includes a scintillator and such like, converts the emitted radiation into light of other wavelengths such as visible light with the scintillator and obtains image data from the radiation detection elements. However, the radiation imaging apparatus may be a direct type apparatus which directly detects radiation with the radiation detection elements, not via the scintillator and such like.

Figure 3:
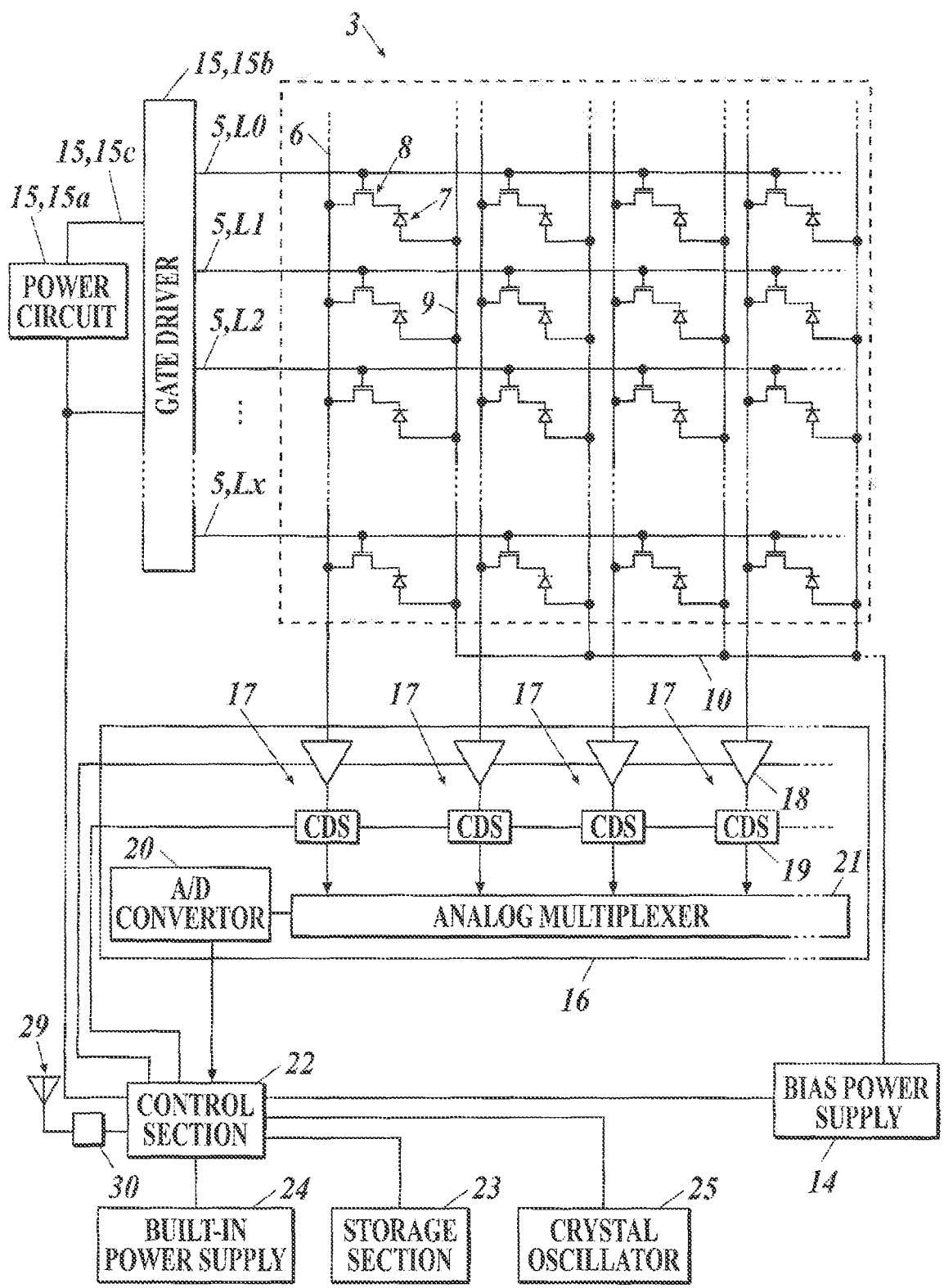
FIG. 3 is a block diagram showing a functional configuration of an FPD cassette in first and second embodiments.

FIG. 3 is a block diagram showing an equivalent circuit of the FPD cassette 3. As shown in FIG. 3, the FPD cassette 3 has a plurality of radiation detection elements 7 which are two-dimensionally (matrix pattern) disposed on a sensor substrate not shown in the drawings (detection section). Each of the radiation detection elements 7 accumulates electric charges corresponding to the amount of emitted radiation. The radiation detection elements 7 are connected to respective bias lines 9, and the bias lines 9 are connected to a connection 10. The connection 10 is connected to a bias power supply 14, and reverse bias voltage is applied to the radiation detection elements 7 via the respective bias lines 9 from the bias power supply 14.

The radiation detection elements 7 are connected to respective thin film transistors (hereinafter, referred to as TFTs) 8 as switch elements, and the TFTs 8 are connected to signal lines 6. In a scanning drive section 15, on voltage and off voltage supplied from a power circuit 15a via a wiring 15c are switched in a gate driver 15b and applied to lines L0 to Lx of scanning lines 5. When the on voltage is applied via the scanning lines 5, the TFTs 8 are turned on and release the electric charges accumulated in the radiation detection elements 7 to the signal lines 6. When the off voltage is applied via the scanning lines 5, the TFTs 8 are turned off and interrupt the conduction between the radiation detection elements 7 and the signal lines 6 to accumulate, in the radiation detection elements 7, the electric charges generated in the radiation detection elements 7. The radiation detection elements 7 and the TFTs 8 connected thereto form pixels.

A plurality of reading circuits 17 is provided in a reading IC 16, and the reading circuits 17 are connected to respective signal lines 6. In reading processing of image data, when the electric charges are released from the radiation detection elements 7, the electric charges flow into the reading circuits 17 via the signal lines 6, and voltage values corresponding to the amount of electric charges flowed into the respective reading circuits 17 are output by amplifier circuits 18. Correlated double sampling circuits (each described as "CDS" in FIG. 3) 19 read out the voltage values output from the amplifier circuits 18 as image data of analog values, and output the image data downstream. The output image data is sequentially transmitted via an analog multiplexer 21 to an A/D converter 20, sequentially converted into image data of digital values by the A/D convertor 20 and output to a storage section 23 to be sequentially stored.

The control section 22 is configured by including a computer, an FPGA (Field Programmable Gate Array) or the like (not shown in the drawings) in which a CPU (Central Processing Unit), a ROM (Read Only Memory), a RAM (Random Access Memory), an input output interface and such like are connected to a bus. The control section 22 may be formed of a dedicated control circuit. The control section 22 is connected to the storage section 23 which is configured by including a SRAM (Static RAM), a SDRAM (Synchronous DRAM), a NAND type flash memory and such like. The control section 22 is also connected to a wireless communication section 30 which performs wireless communication with external equipment such as the radiation control apparatus 1 via an antenna 29. Since the radiation control apparatus 1 communicates with the FPD cassette 3 wirelessly, it is not necessary to connect the radiation control apparatus 1 with the FPD cassette 3 by a cable or the like when performing imaging during doctor's rounds, which is very convenient.

The control section 22 is connected to a built-in power supply 24 or the like which supplies necessary electric power to functional sections such as the scanning drive section 15, reading circuits 17, storage section 23 and bias power supply 14. The control section 22 controls operations of the above-mentioned scanning drive section 15 and reading circuits 17 to make the radiation detection elements 7 accumulate electric charges corresponding to the radiation amount, release the accumulated electric charges to the signal lines 6 and to read out the released electric charges as image data by the reading circuits 17, for example.

The control section 22 is further connected to the crystal oscillator 25. The crystal oscillator 25 is an element which oscillates by piezoelectric effect, and the oscillation number is input to the CPU of control section 22. The control section 22 measures time on the basis of the oscillation number which is input from the crystal oscillator 25.

Though the FPD cassette 3 may be brought by an imaging operator such as a radiological technician, the FPD cassette 3 can be conveyed by being inserted into a cassette pocket 11 provided in the radiation control apparatus 1 as the mobile cart for doctor's rounds since the FPD cassette 3 is relatively heavy and is possibly broken or becomes out of order when it falls.

(Operation of Radiation Imaging System 100)

Next, the imaging operation in the radiation imaging system 100 will be described.

First, the imaging operator performs preparation for imaging. For example, the imaging operator inputs (sets) radiation emission conditions via the operation section 102 in the radiation control apparatus 1. The radiation emission conditions include a tube current, a tube voltage, a frame rate (number of frame images captured per unit time (1 second)), a total imaging time for one imaging, a total number of frame images to be captured for one imaging, type of additional filter and radiation emission time per frame image, for example. The imaging operator also performs positioning of the subject H, radiation source 2 and the FPD cassette 3.

When the preparation for imaging is completed, the imaging operator presses the first-step switch of exposure switch 102a. When the first-step switch of exposure switch 102a is pressed, the control section 101 of the radiation control apparatus 1 activates the radiation source 2 and transmits an activation signal to the FPD cassette 3 via the antenna 108 by the wireless communication section 106. When the wireless communication section 30 receives the activation signal, the control section 22 of FPD cassette 3 sequentially applies the on voltage from the gate driver 15b (see FIG. 3) of scanning drive section 15 to the lines L1 to Lx of scanning lines 5, and performs reset processing of the radiation detection elements 7 of removing the electric charges remaining in the radiation detection elements 7 by releasing the electric charges to the signal lines 6, for example. When the reset processing is finished, the control section 22 applies the off voltage from the gate driver 15b to the lines L1 to Lx of scanning lines 5, and shifts to an electric charge accumulation state. The control section 22 transmits an interlock release signal to the radiation control apparatus 1 by the wireless communication section 30.

When the second-step switch of exposure switch 102a is pressed, the control section 101 of the radiation control apparatus 1 determines whether the interlock release signal from the FPD cassette 3 is received by the wireless communication section 106. If the control section 101 does not determine that the interlock release signal is received, the control section 101 stands by for reception of interlock release signal. When the interlock release signal is received, on the basis of the set radiation emission conditions, the control section 101 calculates radiation emission time to emit radiation by the radiation source 2 and reading start time to start reading by the FPD cassette 3 for generating frame images of dynamic imaging. The control section 101 transmits the reading start time to the FPD cassette 3 by the wireless communication section 106. The control section 101 controls the drive section 105 to perform radiation emission (pulse emission) on the radiation emission conditions set in the radiation source 2 on the basis of the calculated radiation emission time.

When the reading start time transmitted from the radiation control apparatus 1 arrives, the control section 22 in the FPD cassette 3 sequentially applies the on voltage from the gate driver 15b to the lines L0 to Lx of the scanning lines 5 to perform reading processing of image data of frame images as mentioned above. When the reading processing of line Lx is finished, the control section 22 performs re-reading of electric charges in the radiation detection elements 7 for a single line, and determines whether or not an electric charge amount of the re-read electric line is a predetermined threshold or more. The predetermined threshold may be compared with a representative value (for example, average value) of electric charge amounts of a plurality of pixels of the re-read line, or the predetermined threshold may be compared with an electric charge amount of a single pixel.

FIG. 4A shows the operation of FPD cassette 3, read electric charge amount and radiation tube voltage in a normal case (that is, when there is no synchronization deviation between the radiation emission period and the electric charge accumulation period) in the first embodiment. FIG. 4B shows the operation of FPD cassette 3, read electric charge amount and radiation tube voltage when there is the synchronization deviation between the radiation emission period and the electric charge accumulation period (when the radiation emission period is delayed). Each of FIGS. 4A and 4B shows an example in which the electric charges of radiation detection elements 7 on the line L0 (Line 0) are re-read after the reading of electric charges of radiation detection elements 7 of lines L0 to Lx is finished.

As shown in FIG. 4A, when there is no synchronization deviation between the radiation emission period and the electric charge accumulation period, the electric charges in the radiation detection elements 7 of the re-read line L0 are nearly 0. However, as shown in FIG. 4B, when the end of radiation emission period is shifted afterwards to cross the reading period in a case where the time measured by the radiation control apparatus 1 is delayed with respect to the time measured by the FPD cassette 3 or in a case where fluctuation is generated in the radiation output of radiation source 2, for example, the electric charges corresponding to the radiation emitted in the reading period are accumulated in the radiation detection elements 7. Thus, when the electric charges in the radiation detection elements 7 of the line L0 are re-read, the detected amount of electric charges is a predetermined threshold or more.

If it is not determined that the electric charge amount of the re-read line is the predetermined threshold or more, the control section 22 determines that there is no synchronization deviation between the radiation emission period and the electric charge accumulation period, and continues the imaging sequence. If it is determined that the electric charge amount of the re-read line is the predetermined threshold or more, the control section 22 determines that there is synchronization deviation between the radiation emission period and the electric charge accumulation period, and continues the imaging sequence after adjusting the synchronization deviation on the basis of the electric charge amount of the re-read line.

Though FIG. 4B shows, as an example, a case where the radiation emission period is delayed with respect to the electric charge accumulation period, there is a case where the radiation emission period is advanced with respect to the electric charge accumulation period. Also in this case, the electric charge amount of the re-read line (or pixel) is the predetermined value or more. In many cases, the tendency of radiation emission period to be advanced or delayed with respect to the electric charge accumulation period is known in advance according to the characteristics of crystal oscillators of radiation control apparatus 1 and FPD cassette 3 and the radiation output characteristic of the radiation source 2.

Thus, in a case where it is known that the radiation emission period tends to be delayed with respect to the electric charge accumulation period, for example, as shown in FIG. 4B, the control section 22 adjusts the synchronization deviation between the radiation emission period and the electric charge accumulation period by extending the electric charge accumulation period for generating the next frame image or providing a waiting time before the start timing of accumulation for the next frame image. The reading start time for each of the frame images which have not yet been captured is delayed for the amount of the extension of accumulation time or the waiting time with respect to the time notified from the radiation control apparatus 1.

In a case where it is known that the radiation emission period tends to be advanced with respect to the electric charge accumulation period, the control section 22 shortens the electric charge accumulation period for the next frame image. The reading start time for each of the frame images which have not yet been captured is advanced for the shortened amount of the accumulation time with respect to the time notified from the radiation control apparatus 1.

The control section 22 repeatedly executes the above accumulation and reading processing to all the frame images, and generates a plurality of frame images forming the dynamic image of the subject H.

As described above, when the reading start time transmitted from the radiation control apparatus 1 arrives, the control section 22 of the FPD cassette 3 sequentially applies the on voltage from the gate driver 15b to the lines L0 to Lx of the scanning lines 5 and performs reading processing of image data. When the reading processing of line Lx is finished, the control section 22 performs re-reading of electric charges in the radiation detection elements 7 for a single line and determines whether there is synchronization deviation between the radiation emission period and the electric charge accumulation period on the basis of the electric charge amount of the re-read line. If there is the synchronization deviation, the control section 22 adjusts the synchronization deviation. Accordingly, it is possible to suppress the deterioration of image quality due to the synchronization deviation between the radiation emission period and the electric charge accumulation period.

Second Embodiment

Next, a second embodiment will be described.

The configuration of radiation imaging system in the second embodiment is similar to that of radiation imaging system 100 described in the first embodiment, and thus the explanation thereof is omitted. An operation in the second embodiment will be described.

In the first embodiment, electric charges in the radiation detection elements 7 are re-read for a single line each time the reading of electric charges in the radiation detection elements 7 for generating a frame image is finished. Then, the synchronization deviation between the radiation emission period and electric charge accumulation period is adjusted on the basis of electric charge amount in the radiation detection elements 7 of the re-read single line. In the second embodiment, the re-reading of electric charge amount in the radiation detection elements 7 is performed for a plurality of lines each time the reading of electric charges from the radiation detection elements 7 for generating a frame image is finished. Then, the synchronization deviation is adjusted on the basis of electric charge amount in the radiation detection elements 7 for the re-read plurality of lines. The operation of radiation imaging system 100 is similar to that of the first embodiment until the arrival of reading start time in the FPD cassette 3, the reading start time being transmitted from the radiation control apparatus 1. Thus, the explanation thereof is omitted.

When the reading start time transmitted from the radiation control apparatus 1 arrives in the FPD cassette 3, the control section 22 sequentially applies on voltage to the lines L0 to Lx of scanning lines 5 from the gate driver 15b and performs reading processing of image data for a frame image as described above. When the reading processing of line Lx is finished, the control section 22 re-reads electric charges from the radiation detection elements 7 of a plurality of lines, and determines whether the electric charge amount in each of the re-read lines is a predetermined threshold or more. The predetermined threshold may be compared with a representative value (for example, average value) of electric charge amounts in a plurality of pixels of the re-read line, or the predetermined threshold may be compared with an electric charge amount of a single pixel.

FIG. 5A shows the operation of FPD cassette 3, read electric charge amount and radiation tube voltage in a normal case (that is, when there is no synchronization deviation between the radiation emission period and electric charge accumulation period) in the second embodiment. FIG. 5B shows the operation of FPD cassette 3, read electric charge amount and radiation tube voltage when there is synchronization deviation between the radiation emission period and electric charge accumulation period (when the radiation emission period is advanced with respect to the electric charge accumulation period) in the second embodiment. Each of FIGS. 5A and 5B illustrates an example in which re-reading of electric charges is performed for the radiation detection elements 7 of lines L0 to L1 (Line 0 and Line 1) after the reading of lines L0 to Lx is finished.

As shown in FIG. 5A, when there is no synchronization deviation between the radiation emission period and the electric charge accumulation period, the electric charge amounts in the radiation detection elements 7 of the re-read lines L0 and L1 are nearly 0. However, as shown in FIG. 5B, in a case where the start of radiation emission period is shifted to be earlier such as a case where the time measured in the radiation control apparatus 1 is advanced with respect to the time measured in the FPD cassette 3 and a case where fluctuation is generated in the radiation output of radiation source 2, the electric charges are already stored in the radiation detection elements 7 at the start time of electric charge accumulation period for generating the next frame image. In addition, as shown in FIG. 4B, in a case where the radiation emission period is shifted afterwards with respect to the electric charge accumulation period and crosses the reading period, the electric charges corresponding to the radiation emitted in the reading period are accumulated in the radiation detection elements 7. Thus, the amount of detected electric charges is a predetermined threshold or more when the electric charges are re-read from the radiation detection elements 7 of the plurality of lines such as the lines L0 and L1.

If it is not determined that the electric charge amount of the re-read plurality of lines is the predetermined threshold or more, the control section 22 determines that there is no synchronization deviation between the radiation emission period and the electric charge accumulation period, and continues the imaging sequence.

If it is determined that the electric charge amount of the re-read plurality of lines is the predetermined threshold or more, the control section 22 determines whether the radiation emission period is delayed or advanced with respect to the electric charge accumulation period on the basis of the electric charge amounts of re-read plurality of lines. On the basis of the determination result, the control section 22 adjusts synchronization between the radiation emission period and electric charge accumulation period and continues the imaging sequence after the adjustment.

Specifically, among the electric charge amounts of the re-read plurality of lines, if the electric charge amount of one re-read line is larger than the electric charge amount of a re-read line which was re-read earlier than the one re-read line (for example, in a case shown in FIG. 5B), the control section 22 determines that the radiation emission period is advanced with respect to the electric charge accumulation period, and adjusts the synchronization deviation between the radiation emission period and electric charge accumulation period by shortening the electric charge accumulation period for generating the next frame image. The reading start time for each of the frame images which have not yet been captured is advanced for the shortened amount of the accumulation time with respect to the time notified from the radiation control apparatus 1.

Among the electric charge amounts of the re-read plurality of lines, if the electric charge amount of one re-read line is smaller than the electric charge amount of a re-read line which was re-read earlier than the one re-read line, the control section 22 determines that the radiation emission period is delayed with respect to the electric charge accumulation period, and adjusts the synchronization deviation between the radiation emission period and electric charge accumulation period by extending the electric charge accumulation period for generating the next frame image or by providing a waiting time before the accumulation start timing for generating the next frame image. The reading start time for each of the frame images which have not yet been captured is delayed for the amount of extension of electric charge accumulation period or the amount of waiting time with respect to the time notified from the radiation control apparatus 1.

The control section 22 repeatedly executes the accumulation and reading processing for all the frame images and generates the plurality of frame images forming the dynamic image of subject H.

In such way, when the reading start time transmitted from the radiation control apparatus 1 arrives, the control section 22 of FPD cassette 3 sequentially applies on voltage to lines L0 to Lx of scanning lines 5 from the gate driver 15b and performs reading processing of image data of a frame image. When the reading processing of line Lx is finished, the control section 22 preforms re-reading of the radiation detection elements 7 of a plurality of lines and determines whether there is synchronization deviation between the radiation emission period and electric charge accumulation period on the basis of the electric charge amounts of the plurality of re-read lines. If it is determined that there is synchronization deviation, the control section 22 determines whether the electric charge accumulation period is delayed or advanced with respect to the radiation emission period on the basis of the electric charge amounts of the plurality of re-read lines, and adjusts the synchronization deviation on the basis of the determination result.

Accordingly, in the second embodiment, the synchronization deviation can be adjusted by determining whether the electric charge accumulation period is delayed or advanced with respect to the radiation emission period for each frame. Thus, it is possible to suppress the deterioration of image quality due to the synchronization deviation between the radiation emission period and the electric charge accumulation period even when the direction of synchronization deviation is not constant.

Third Embodiment

Next, the third embodiment of the present invention will be described.

Figure 6:
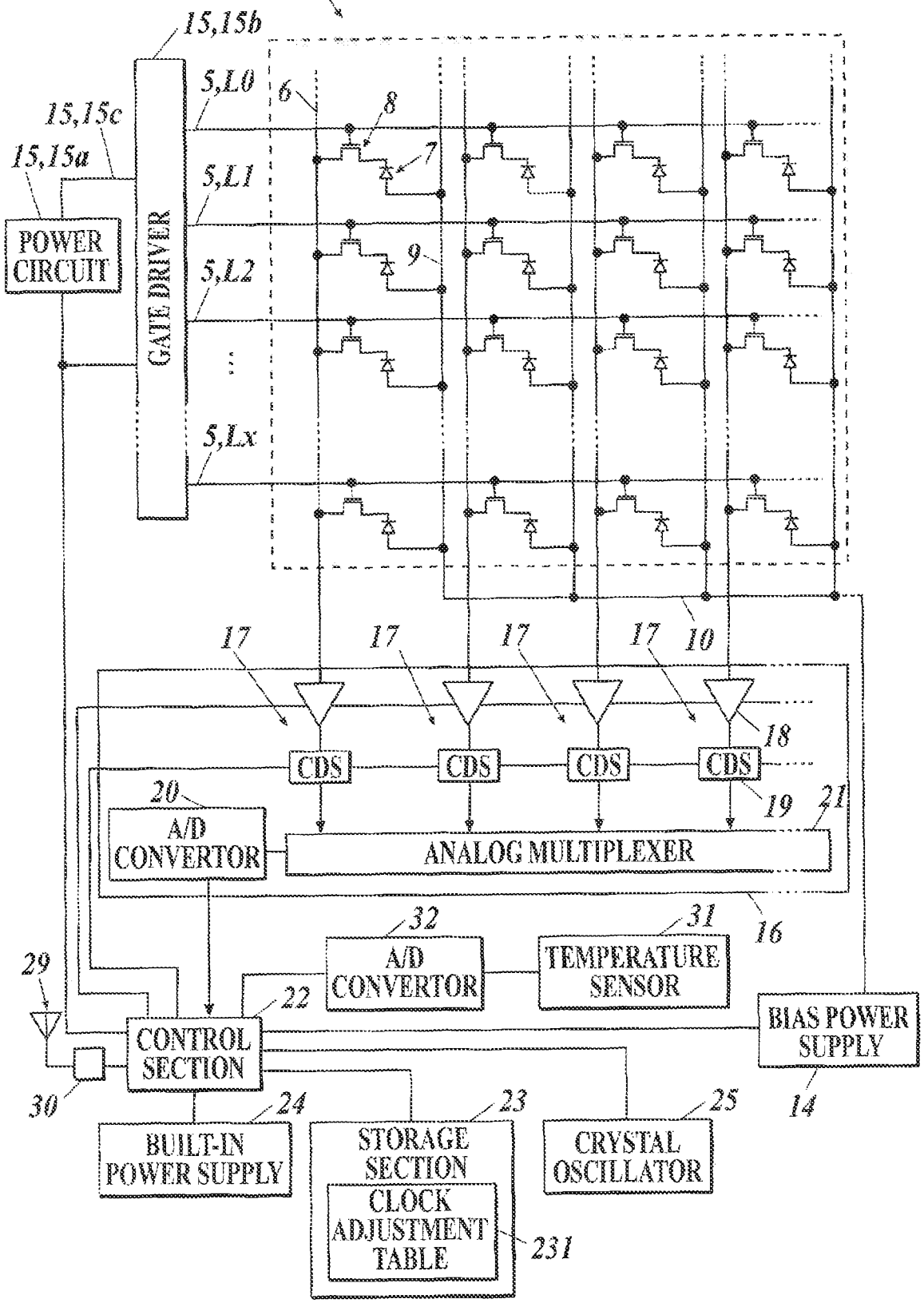
FIG. 6 is a block diagram showing a functional configuration of the FPD cassette in a third embodiment.

FIG. 6 is a block diagram showing an equivalent circuit of FPD cassette 3A in the third embodiment. As shown in FIG. 6, the FPD cassette 3A in the third embodiment includes, in addition to the configuration of FPD cassette 3 described in the first embodiment, a temperature sensor 31 which detects the temperature inside the housing of FPD cassette 3A and an A/D convertor 32 which converts a voltage output from the temperature sensor 31 into a digital voltage value and outputs the converted value to the control section 22.

The storage section 23 stores a clock adjustment table 231.

The frequency characteristic of vibration of crystal oscillator 25 with respect to temperature is represented by a quadratic curve protruding upward with an apex at 25° C., and the frequency is lower as the temperature difference from 25° C. is larger. The clock adjustment table 231 is a table in which a reference temperature is set to be 25° C. having the maximum operation frequency of crystal oscillator 25, and each temperature difference from the reference temperature is associated with the oscillation number of crystal oscillator 25 corresponding to 1 unit time (for example, 1 second) for the temperature difference on the basis of the frequency characteristic of crystal oscillator 25.

The other configuration of FPD cassette 3A is similar to that of FPD cassette 3 described in the first embodiment, and thus, the explanation thereof is omitted.

Next, the operation in the third embodiment will be described.

Figure 7:
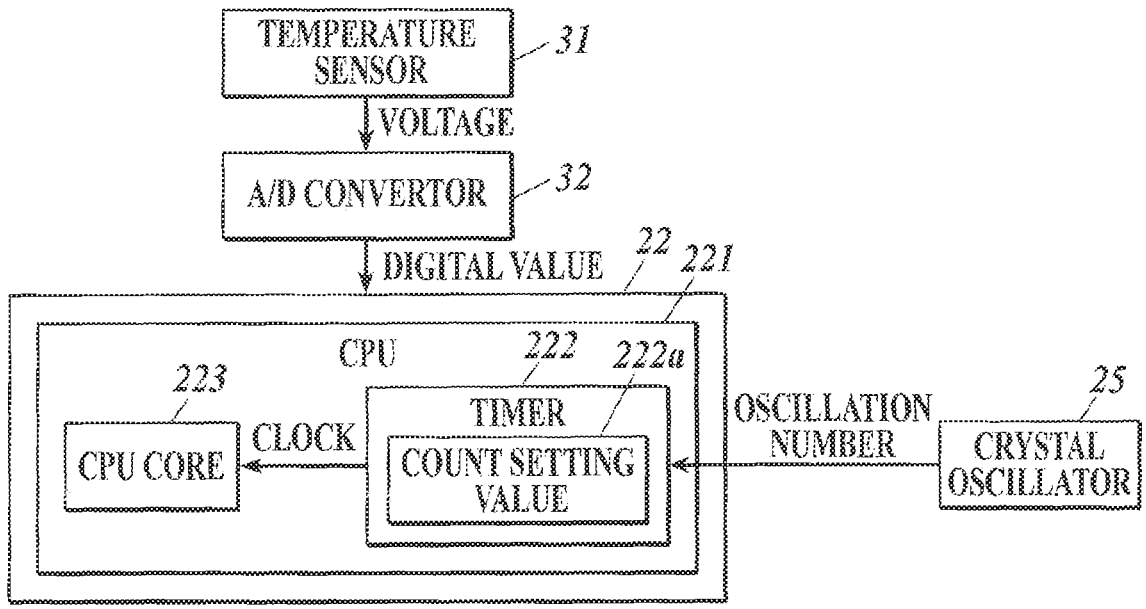
FIG. 7 is a block diagram showing information flow according to measurement and adjustment of time of the control section of FIG. 6.

FIG. 7 is a block diagram showing the information flow of measurement and adjustment of time in the control section 22.

As shown in FIG. 7, the oscillation number of crystal oscillator 25 is input to a timer 222 in the CPU 221 of the control section 22. The oscillation number (count setting value 222a) corresponding to 1 unit time (for example, 1 second) is set in a register in the timer 222, and the timer 222 outputs the clock to a CPU core 223 each time the set oscillation number is counted. The CPU core 223 measures time on the basis of the clock from the timer 222. At the time of introduction into the facility, the clock is corrected at a predetermined temperature (that is, 25° C.) at which the crystal oscillator 25 has a maximum operation frequency. The same applies to the measurement and correction of time in the radiation control apparatus 1.

However, in many cases, the FPD cassette 3A is used in an environment in which heat is kept and the temperature easily rises such as between a sheet and a patient lying on a bed, and thus, the heat release possibly cannot be ensured sufficiently. On the other hand, the radiation control apparatus 1 naturally releases sufficient heat with respect to the heat generation amount thereof even during operation, and thus the influence of heat generation is negligible. Thus, even when the times are synchronized between the radiation control apparatus 1 and the FPD cassette 3A in advance, the times are shifted from each other in some cases due to the influence of change in operation frequency of crystal oscillator 25 caused by temperature rise of the FPD cassette 3A.

Figure 8:
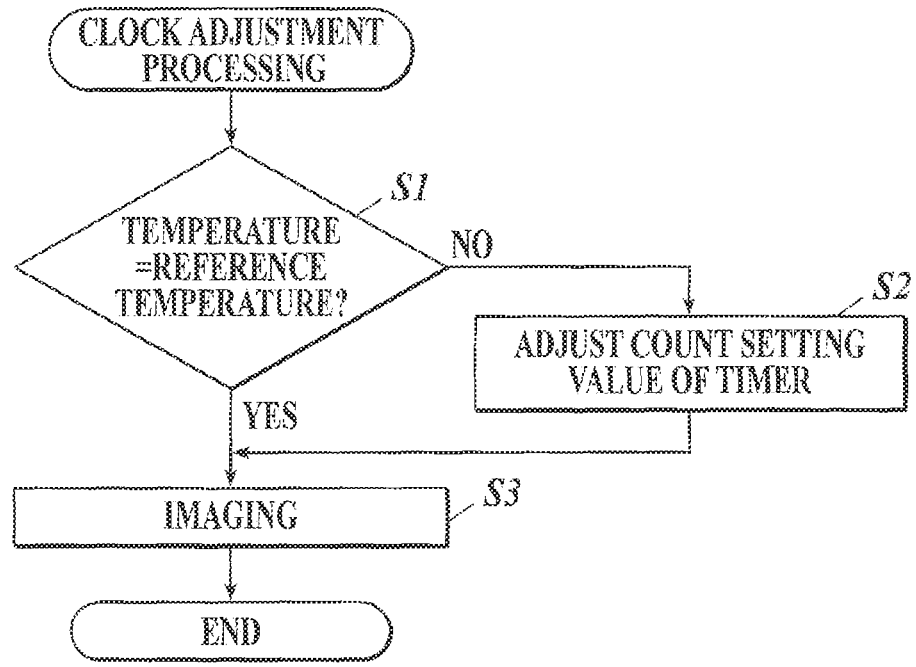
FIG. 8 is a flowchart showing clock adjustment processing executed by the control section of FIG. 6.

In the third embodiment, the control section 22 executes clock adjustment processing (see FIG. 8) immediately before imaging. For example, when the pressing of first-step switch of the exposure switch 102a is detected in the radiation control apparatus 1 and the activation signal is transmitted to the FPD cassette 3A via the antenna 108 (when the activation signal is received by the wireless communication section 30), the control section 22 of the FPD cassette 3A performs reset processing and executes clock adjustment processing shown in FIG. 8.

In the clock adjustment processing, the control section 22 first obtains a temperature value from the temperature sensor 31, and determines whether the obtained temperature is equal to a reference temperature (here, 25° C. which is the predetermined temperature having the maximum operation frequency) (step S1).

If it is determined that the temperature obtained from the temperature sensor 31 is equal to the reference temperature (step S1; YES), the control section 22 executes imaging (step S3).

If it is not determined that the temperature obtained from the temperature sensor 31 is equal to the reference temperature (step S1; NO), the control section 22 adjusts the timer 222 by reading out the oscillation number corresponding to the temperature difference between the obtained temperature and the reference temperature from the clock adjustment table 231, and updating the count setting value 222a of the timer 222 with the read value (step S2). After the adjustment, the control section 22 executes imaging (step S3).

In step S3, the control section 22 stands by for the end of reset processing. When the reset processing is finished, the control section 22 shifts the state to the electric charge accumulation state by applying the off voltage to the lines L1 to Lx of scanning lines 5 from the gate driver 15b. The wireless communication section 30 transmits the interlock release signal to the radiation control apparatus 1. When the reading start time by the FPD cassette 3A is received from the radiation control apparatus 1 and the reading start time arrives, the control section 22 sequentially applies the on voltage to the lines L0 to Lx of the scanning lines 5 from the gate driver 15b and performs reading processing of image data as mentioned above. When the reading of line Lx is finished, the control section 22 shifts to the accumulation state for generating the next frame image, and accumulates the electric charges corresponding to the radiation emitted from the radiation source 2. When the reading start time arrives, the control section 22 sequentially applies the on voltage to the lines L0 to Lx of scanning lines 5 from the gate driver 15b and performs image data reading processing as mentioned above. The control section 22 repeatedly executes accumulation and reading processing for all the frame images and generates the radiation image of the subject.

As described above, the control section 22 of the FPD cassette 3A obtains the temperature from the temperature sensor 31 immediately before the start of imaging, and if the obtained temperature is not equal to the reference temperature, the control section 22 performs clock adjustment of the timer 222 and shifts to imaging after the adjustment. Accordingly, it is possible to suppress the deterioration of image quality due to the synchronization deviation between the radiation emission period and the electric charge accumulation period caused by the clock shift due to the influence of temperature.

As described above, the control section 22 of FPD cassette 3 in the radiation imaging system 100 adjusts the synchronization timing of radiation source 3 and FPD cassette 3 by using the waveform of radiation emitted from the radiation source 3, the waveform being obtained by reading out the electric charges from at least a part of the plurality of radiation detection elements 7. For example, the control section 22 re-reads the electric charges from a part of the plurality of radiation detection elements 7 after reading out electric charges from the plurality of radiation detection elements 7 for generating one frame image of the dynamic image, and determines whether radiation was emitted during a period other than the electric charge accumulation period of radiation detection elements 7 on the basis of the electric charge amount of the re-read radiation detection elements 7. If it is determined that the radiation was emitted during a period other than the electric charge accumulation period of radiation detection elements 7, the control section 22 adjusts the electric charge accumulation period so as to emit radiation within the electric charge accumulation period when the next frame image is generated. Accordingly, it is possible to suppress the deterioration of image quality due to the synchronization deviation between the radiation emission period in the radiation source 2 and the electric charge accumulation period in the FPD cassette 3.

For example, the control section 22 of FPD cassette 3 re-reads electric charges from the radiation detection elements 7 of a plurality of lines. If an electric charge amount of a re-read line is a predetermined value or more and an electric charge amount of one re-read line is larger than an electric charge amount of a re-read line which was re-read earlier than the one re-read line, the control section 22 determines that the radiation emission period is advanced with respect to the electric charge accumulation period, and shortens the electric charge accumulation period for generating the next frame image. Accordingly, in a case where the radiation emission period is advanced with respect to the electric charge accumulation period, it is possible to detect the advance and adjust so that radiation is emitted within the electric charge accumulation period when the next frame image is generated.

If the electric charge amount of the re-read line is a predetermined value or more and the electric charge amount of the one re-read line is smaller than the electric charge amount of the re-read line which was re-read earlier than the one re-read line, the control section 22 of the FPD cassette 3 determines that the radiation emission period is delayed with respect to the electric charge accumulation period, and extends the electric charge accumulation period for generating the next frame image or provides a waiting time before start of the electric charge accumulation period. Accordingly, in a case where the radiation emission period is delayed with respect to the electric charge accumulation period, it is possible to detect the delay and adjust so that radiation is emitted within the electric charge accumulation period when the next frame image is generated.

The descriptions of the embodiments are preferred examples of the present invention, and the present invention is not limited to the examples. The detailed configurations and detailed operations of the apparatuses forming the radiation imaging system can be appropriately modified within the scope of the present invention.

What is claimed is:

1. A portable radiation imaging apparatus comprising:
   a detection section which includes a plurality of radiation detection elements for accumulating electric charges corresponding to a radiation amount, the radiation detection elements being two-dimensionally arranged; and
   a control section which controls, by a synchronization timing between a radiation source and the detection section that is determined in advance, accumulation of the electric charges in the radiation detection elements and reading of the accumulated electric charges from the radiation detection elements using reading circuits, and generates a plurality of frame images of a subject, the electric charges to be accumulated corresponding to the radiation amount of x-ray radiation emitted in a pulsed manner by the radiation source and transmitted through the subject, wherein
   the control section adjusts a deviation of the synchronization timing between the radiation source and the detection section based on the radiation amount.

2. The radiation imaging apparatus according to claim 1, wherein, after the reading of the electric charges from the plurality of radiation detection elements for generating a frame image of the plurality of frame images, the control section re-reads electric charges from a part of the plurality of radiation detection elements, and determines whether radiation is emitted during a period other than an electric charge accumulation period of the radiation detection elements on the basis of the radiation amount of a re-read radiation detection element, and when the control section determines that radiation is emitted before or after the electric charge accumulation period of the radiation detection elements, the control section adjusts the electric charge accumulation period so that radiation is emitted within the electric charge accumulation period when a next frame image is generated.

3. The radiation imaging apparatus according to claim 2, wherein, when the radiation amount of the re-read radiation detection element is a predetermined value or more, the control section determines that radiation is emitted before or after the electric charge accumulation period of the radiation detection elements.

4. The radiation imaging apparatus according to claim 2, wherein, the control section re-reads electric charges from radiation detection elements of a plurality of lines, and when the radiation amount of a re-read line is a predetermined value or more and the radiation amount of one re-read line is larger than an electric charge amount of a line which is re-read earlier than the one re-read line, the control section determines that the radiation emission period is advanced with respect to the electric charge accumulation period, and shortens the electric charge accumulation period when the next frame image is generated.

5. The radiation imaging apparatus according to claim 2, wherein, the control section re-reads electric charges from radiation detection elements of a plurality of lines, and when the radiation amount of a re-read line is a predetermined value or more and the radiation amount of one re-read line is smaller than an electric charge amount of a line which is re-read earlier than the one re-read line, the control section determines that the radiation emission period is delayed with respect to the electric charge accumulation period, and extends the electric charge accumulation period or provides a waiting time before start of the electric charge accumulation period when the next frame image is generated.

6. A radiation imaging system comprising:
   a radiation source which is capable of pulse emission; and
   the radiation imaging apparatus according to claim 1.

7. The radiation imaging apparatus according to claim 1, wherein the control section reads electric charges based on the radiation amount from the radiation detection elements of a plurality of lines, and adjusts the deviation of the synchronization timing between the radiation source and the detection section based on the radiation amount.

8. The radiation imaging apparatus according to claim 1, wherein, the control section adjusts the deviation of the synchronization timing between the radiation source and the detection section based on an inclination of the radiation amount.

9. The radiation imaging apparatus according to claim 8, wherein, the control section adjusts the deviation of the synchronization timing between the radiation source and the detection section based on a difference of the electric charge amount of two read lines.

\* \* \* \* \*